United States Patent [19]

Bro et al.

[11] Patent Number: 4,677,985
[45] Date of Patent: Jul. 7, 1987

[54] APPARATUS AND METHOD FOR DETERMINING INTRACRANIAL PRESSURE AND LOCAL CEREBRAL BLOOD FLOW

[76] Inventors: William J. Bro, 3735 W. Cavalier Dr., Phoenix, Ariz. 85019; L. Philip Carter, 2910 N. 3rd Ave., Phoenix, Ariz. 85013

[21] Appl. No.: 764,496
[22] Filed: Aug. 12, 1985
[51] Int. Cl.$^4$ .............................................. A61B 5/02
[52] U.S. Cl. .................................... 128/691; 128/748
[58] Field of Search ............................... 128/691–692, 128/736, 670–671, 748

[56] References Cited

U.S. PATENT DOCUMENTS

| | | | |
|---|---|---|---|
| 4,062,354 | 12/1977 | Taylor et al. | 128/748 X |
| 4,186,728 | 2/1980 | Van Lotringen | 128/748 X |
| 4,206,762 | 6/1980 | Cosman | 128/748 X |
| 4,246,908 | 1/1981 | Inagaki et al. | 128/748 |
| 4,312,361 | 1/1982 | Nicholson et al. | 128/748 |
| 4,354,504 | 10/1982 | Bro | 128/691 |
| 4,393,878 | 7/1983 | Kahn | 128/748 |
| 4,403,615 | 9/1983 | Hoehner | 128/692 |
| 4,438,773 | 3/1984 | Letterio | 128/748 |
| 4,502,491 | 5/1985 | Ender et al. | 128/748 X |

OTHER PUBLICATIONS

McFarland et al.; "Telemetry of Regional Tissue Blood Flow Using Hydrogen Clearance"; *Conf. 8th Ann. NE Bioengr. Conf;* 3-1980, pp. 40–43.

*Primary Examiner*—Kyle L. Howell
*Assistant Examiner*—Angela D. Sykes
*Attorney, Agent, or Firm*—Gregory J. Nelson

[57] ABSTRACT

An intracranial probe to monitor both intracranial pressure and blood flow by thermal diffusion and hydrogen clearance techniques. The probe includes a casing or housing having internal bore which houses a reciprocal piston. The casing is provided with pressure port for commuting pressure to a remote pressure monitor. A pair of platinum or platinum alloy plates are associated with the two terminal integrated circuit which produces an output current proportional to the absolute temperature of the probe contact plate with which temperature transducer is associated. One temperature transducer monitors the temperature of the cold plate of the probe and the other monitors that of the hot plate. The signals are processed at a differentially amplified and fed to a monitor. In addition, the current generated by the platinum contact plates provides an input to a hydrogen clearance monitor to simultaneously determine blood flow by this technique.

11 Claims, 6 Drawing Figures

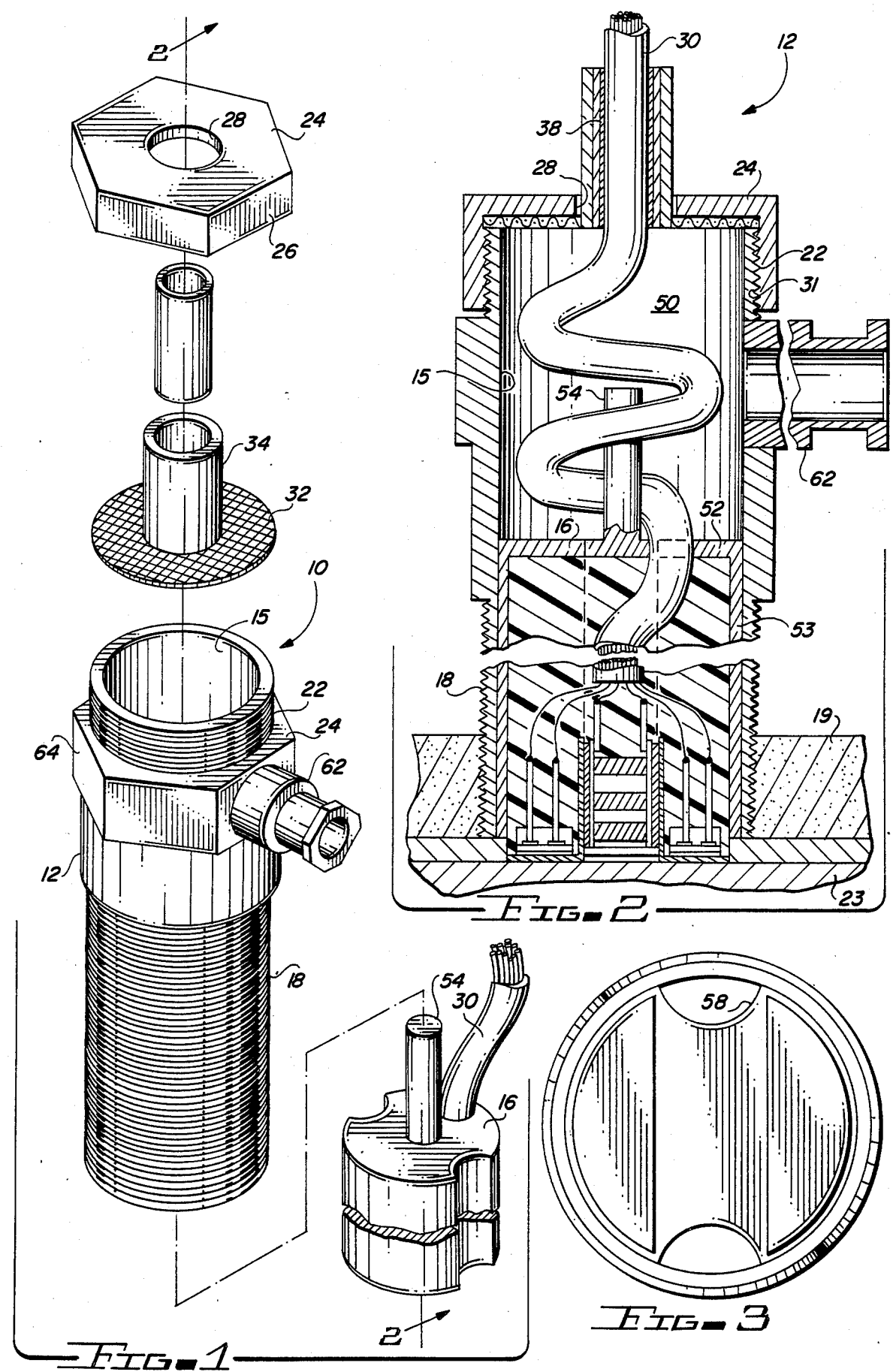

APPARATUS AND METHOD FOR DETERMINING INTRACRANIAL PRESSURE AND LOCAL CEREBRAL BLOOD FLOW

BACKGROUND OF THE INVENTION

This invention relates to a method and apparatus for accurately detecting intracranial pressure and determining local cerebral blood flow by thermal and hydrogen clearance techniques and further relates to a cerebral probe for this purpose.

In the field of cerebrosurgery and neurosurgery, an important adjunct to the assessment and management of the acute head injury patient or the post operative patient is the measurement of intracranial pressure. The brain or cerebrum is protected in a container consisting of the skull and meninges. The container is filled with a fluid which is referred to as the cerebrospinal fluid (abbreviated CSF) and the cerebrum floats in the fluid. An organism membrane referred to as the dura is present inside the skull for maintaining air tightness within the skull. Various conditions such as a blow to the head causes such as an epidermal hemorrage, hydrocephalus and the like may cause an increase in internal pressure in the skull which is mainly attributable to an abnormal condition in the circulatory system of the cerebrospinal fluid. Elevated intracranial pressure is defined as an intracranial pressure (ICP) equal to or greater than 15 Torr using ventriculostomy, a subarachnoid bolt or a subdural catheter.

Internal pressure in the skull has been measured according to various methods. It has been general practice to measure intracranial pressure by epidural transducer methodology which involves drilling a hole in the skull cap and then inserting a tube or probe into a ventricle and breaking the dura to extract a pressure sample and measuring the sample by various pressure sensory techniques.

In more recent developments, pressure transducers of various types have been used for accurately measuring the internal pressure in the skull which has significant advantages in that the dura is not broken and the stress imposed upon the patient is significantly reduced. For example, see U.S. Pat. No. 4,354,504.

In addition to intracranial pressure, other parameters are of value to the physician treating traumatic or chronic cerebral conditions. One of these is measurement of regional cortical blood flow. Various techniques have been used in the prior art for determining blood flow in body organs particularly the brain including photoelectric plethysmography and light beating spectroscopy. One particularly effective technique is disclosed in U.S. Pat. No. 4,354,504 entitled "Thermal Diffusion Flow Probe". In this patent, a blood flow probe is used which utilizes two integrated circuit transducers each of which produces an output current proportional to the absolute temperature of the probe contact plate with which the temperature transducer is associated. One temperature transducer monitors the temperature of the cold plate of the probe and the other temperature transducer monitors the temperature of the hot plate. Each transducer output signal is transmitted from the probe so that the temperature of the hot plate and of the cold plate may be independently measured. Each of these signals is then input to a differential amplifier and a differential temperature signal is made available to a conventional monitoring device. A signal output by the temperature transducer monitoring the hot plate of the probe is also input to a comparator which level is compared with the reference signal. Should the hot temperature exceed the temperature associated with the reference signal, the comparator will cause the heat pump of the probe to be de-energized until such time as the hot plate temperature is reduced to a safe level. Additional features of the prior invention provide that both the hot and cold contact plates of the blood flow probe shall be at ground potential to eliminate hazardous shocks.

Another method of monitoring blood flow is the hydrogen clearance technique which was introduced in approximately 1965 by Knut Aukland, M.D. and others. Aukland discussed measuring local blood flow in an article entitled "Measurement of Local Blood Flow with Hydrogen Gas" in *Circulation Research,* Volume XIV, February, 1964. Since the detailed report of Aukland and co-workers, this method has been widely used to measure blood flow in diverse tissues including the brain. The method basically employs hydrogen-sensitive polargraphical electrodes of fine platinum wire that develop a current proportional to the partial pressure of hydrogen in surrounding tissue. When hydrogen administration is stopped and its concentration in arterial blood falls to zero, the clearance rate of hydrogen from the tissue is reflected as a proportional declining current from the electrode, is determined by local blood flow.

Hydrogen clearance possesses distinct advantages over other blood flow monitoring techniques. Hydrogen clearance can be determined in any tissue where small electrodes can be inserted. Second, multiple flow determinations can be obtained from the same tissue site over long periods of time unlike many other techniques. Third, blood flow can be estimated from the clearance rate of hydrogen independently of the absolute amplitude of the hydrogen signal. There is, however, some evidence that suggests that hydrogen clearance is not as accurate nor as local in measuring blood flow as generally supposed. Other problems stem from the failure to consider possible sources of error in hydrogen clearance monitoring and the invasive nature of the procedure. Nevertheless, hydrogen clearance is a valid and important approach in measuring blood flow.

Similarly, there is some criticism of the heat clearance method of determining local cerebral blood flow. The major criticism of the heat clearance method has been its lack of reliable quantitation.

SUMMARY OF THE INVENTION

Accordingly, there exists a need in medical science for an acceptable method of monitoring blood flow which is simple and inexpensive and will provide an accurate, reliable, quantitative and repetitive value and which will concurrently monitor intercranial pressure. Accordingly, in accordance with the foregoing, the present invention provides an apparatus and method which includes an intracranial pressure transducer and which also provides a method for monitoring blood flow using a thermal probe and simultaneously employing a calibrating and quantitative measurement by hydrogen clearance techniques. Briefly, in accordance with the present invention, a probe for the simultaneous determination of blood flow and intracranial pressure is provided which includes a casing which is adapted to be threaded into a drilled hole or burr in the human skull. The bore of the plug houses a piston which is connected to a conductor cable. Milled slots are provided in the piston to communicate intracranial pressure with a pressure port in the side of the housing. The piston moves in response to movement of the brain. The thermal diffusion system is housed within the piston and includes a thermal electric heat pump, a platinum heat dissipating plate and a platinum heat absorbing plate. Associated with each plate is a temperature transducer, the output of which is provided to a monitoring output and into the input of a differential amplifier. The temperature differential between the hot and cold plates is proportional to blood flow. In addition, the electrical connections are also provided by the conductor cable to the platinum plates to accomodate their use in a hydrogen clearance blood flow monitoring technique which is used to calibrate and quantify the thermal diffusion technique.

BRIEF DESCRIPTION OF THE DRAWINGS

A more complete understanding of the present invention will be had from the following description, claims and drawings in which:

FIG. 1 is an exploded perspective view of the probe;

FIG. 2 is a sectional view taken through lines 2—2 of FIG. 1;

FIG. 3 is a bottom view of the piston housed within the probe;

DESCRIPTION OF THE PREFERRED EMBODIMENTS

Figures 4, 5:
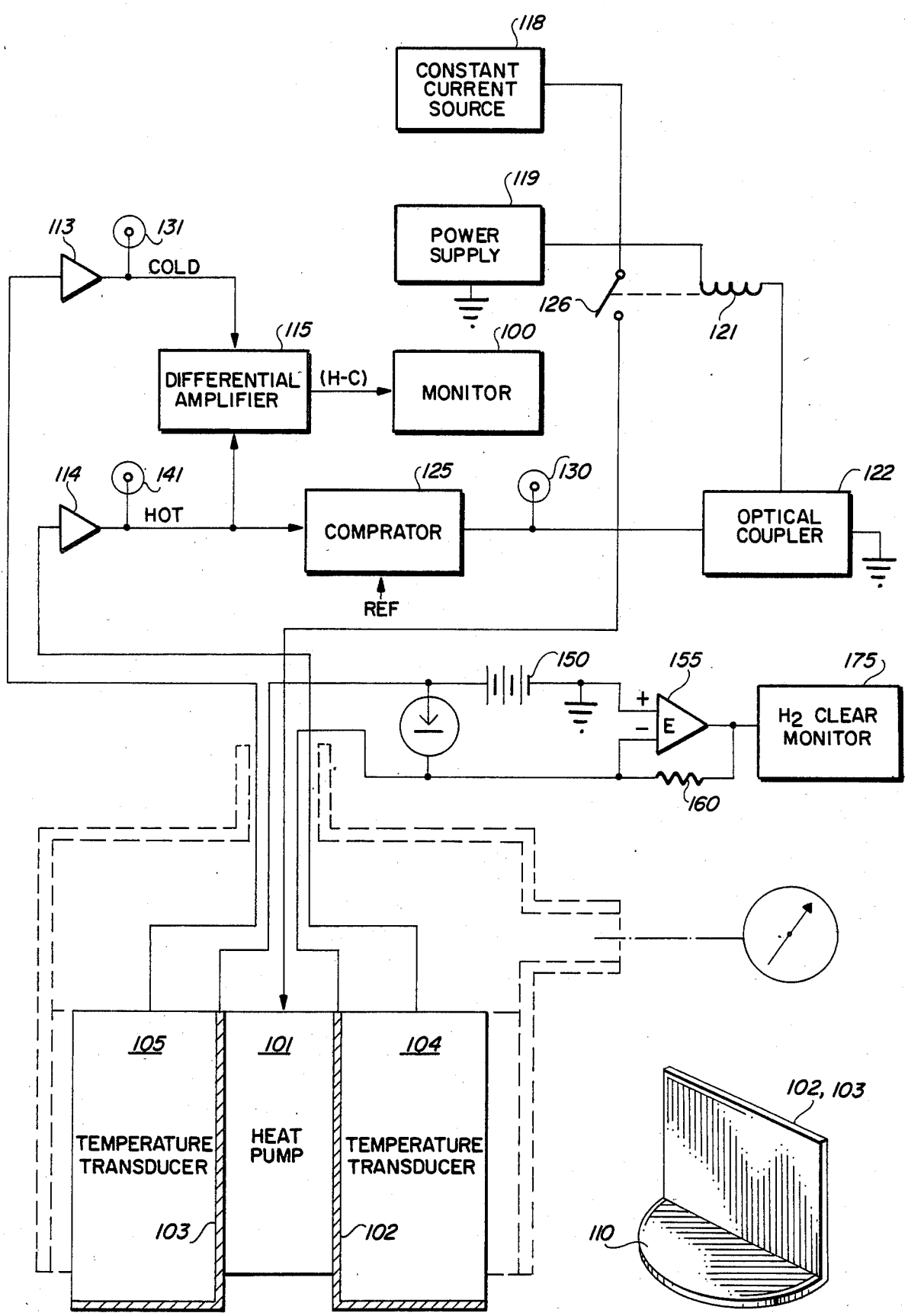
FIG. 4 is a block diagram illustrating the blood flow probe of the invention and the associated electrical components.
FIG. 5 shows the structure of the hot and cold plates of the blood flow probe used for thermal and hydrogen clearance determination.

Turning now to the drawings, particularly FIGS. 1 to 3, the intracranial probe of the present invention is generally designated by the numeral 10 and includes a generally cylindrical casing 12 defining an interior cylindrical bore 15 which houses reciprocal piston 16. The piston diameter may vary however it has been found that a diameter of approximately 0.50" works well. The lower end of the casing exterior is threaded at 18 adapted to be placed in engagement with a burr hole drilled in the skull 19 of the human body as seen in FIG. 2. The thread pattern may be modified for effective engagement with the skull however, typically the casing would be threaded for an axial length approximately ¾ of an inch with 32 threads per inch. The thread depth of ¾ inch is adequate for a standard burr hole drill and allows for different thicknesses of skull bone in the human body. The casing 12 is threaded in the burr hole drilled in the skull of the patient and when inserted will act as a housing to allow both the transmission of the intracranial pressure and insertion of the blood flow monitoring components as will be explained hereafter.

The upper exterior end of the casing 12 is threaded at 22 to receive a cap 24 having an outer hexagonal configuration 26. The hexnut cap 24 is provided with a central aperture 28 to accomodate wire connector 30. Hexnut cap 24 is threaded at 31 for engagement with threads 22 in the housing body. When the cap is in place, a wire mesh washer 32 is interposed between the cap and the upper end of the casing. The washer 32 has a cylindrical center section 34 through which cable 30 passes. Appropriate sealing material may be placed in the area 38 between the washer and the conduit to seal the interior 14 of the housing.

Piston 16 is reciprocable within bore 15 and comprises a generally hollow cylinder having a top 52 and side wall 53. A rod 54 extends axially from the top of the piston within the bore to serve as a guide for the cable 30 which is wrapped about the rod in spiral fashion. The cabling is spiraled in order to allow the piston to move freely in response to movement of the dura 55 as seen in FIG. 2.

As best seen in FIG. 3, an opposed pair of semicircular milled slots 58 approximately 1/16th inch in diameter is provided in the piston side wall to allow intracranial pressure to be transmitted to the interior chamber 50 of the probe and subsequently to pressure port 62 which extends radially from a side wall of the probe casing. The exterior of the casing body is provided with faces 64 shown as hexagonal at the axial location of pressure port to accomodate placement of the probe either manually or with the use of an appropriate surgical tool or wrench. Generally, the casing will be threaded into the skull at threads 18 using the hexagonal surface 64. When the casing is inserted to the proper depth, the piston 16 is inserted into the bore and the casing closed at the hexnut cap 24. The placement of the probe casing without the cap and piston in place permits the surgeon to view the interior of the skull during the securement of the probe. The piston is inserted into the probe interior in contact with the brain surface or dura 23. Thereafter the washer 32 and nut 24 are tightened in place.

Preferably, the casing, piston, nut and washer and all components are made of a surgical grade stainless steel. The thermal probe and the hydrogen clearance probe are formed as an integral part of the piston 16. The thermal probe includes a monitor 100 which may be any conventionally available monitoring device for monitoring and recording the differential temperature of the hot and cold plates of the probe. For example, the monitor 11 may be a Grass Polygraph as manufactured by the Grass Instrument Company of Quincy, Mass.

The thermal probe further includes a thermal electric heat pump 101 such as a heat pump of the type manufactured by Marlow Industries, Model MI1010. Coupled to the heat pump 101 is a heat dissipating plate 102, the hot plate, a heat absorbing plate 103, and the cold plate. Associated with each of the plates 102 and 103 is a temperature transducer 104 and 105, respectively. Typically, the temperature transducers are of the type manufactured by Analog Devices, AD590. The output current of such a device is equal to a scale factor times the temperature of the sensers in degrees Kelvin. Such a device lends itself to remote sensing applications as encountered in applications using a probe to measure blood flow through bodily tissue. Devices of this type provide a high impedance current output and are insensitive to voltage drops over long lines. The output signal of transducers 104 and 105 is transmitted to a remote reading device.

Heat pump 101 is powered by means of a constant current source 118 which typically would be a device such as the MC1566 current regulator manufactured by Motorola powered by power supply 119. An output of the power supply is provided to energize relay coil 121 through optical coupler 122. When relay 121 is energized, normally open contacts 126 close, permitting the current source 118 to drive the heat pump. When an output signal from comparator 125 indicates the signal proportional to the temperature of the hot plate 102 has exceeded the reference temperature signal, the comparator output signal is applied to the optical coupler to break the conduction pump through relay 121 thereby deenergizing the heat pump. This will allow the hot plate 102 to decrease in temperature toward the temperature of the tissue 23 in contact with the plate. The output of the comparator 125 may be observed at a monitoring point 100 to provide a visual or audible alarm indicative of the temperature condition of the hot plate. Accordingly, the temperature of the hot plate will not exceed the safe limit established by the reference signal applied to the comparator.

The hot and cold plates 102 and 103 are thermally coupled to heat pump 101 but are electrically isolated from the heat pump. To reduce the possibility of shock hazard to the patient, plates 102 and 103 and their connection with temperature transducers 104 and 105 are maintained at a power line ground potential.

A signal proportional to the absolute temperature sensed at cold plate 103 by temperature transducer 105 is passed through amplifier 113 and is transmitted to monitoring output 131 as well as to the input of differential amplifier 115. Temperature transducer 104 senses the temperature of hot plate 102 and feeds the output to amplifier 114. The amplifier hot signal is provided to monitoring port 141 and to a second input of differential amplifier 115. The output of the differential amplifier 115 is the differential temperature of hot plate 102 and cold plate 103. With the present invention, the hot and cold temperature may be determined at monitoring ports 131 and 141. Differential temperature signal, HC, is fed from differential amplifier to the input of the monitor 100. At monitor 100 the actual blood flow characteristics at the site of the contact plates 102 and 103 within the piston may be monitored and compared with blood flow characteristics derived from other methods such as hydrogen clearance.

As best seen in FIGS. 4 and 5, contact plates 102 and 103 formed as an integral part of the piston 16 are generally L-shaped in corss-section having a semi-circular horizontal portion 110 positioned at opposite sides of the bottom of the piston 16. Contact plates 102 and 103 are used as the hot and cold plates in the thermal diffusion technique as described above and also as the electrode in the hydrogen clearance technique and thus are made from a noble metal such as platinum or an alloy such as platinum (70%) and iridium (30%). The contact probe components including the transducers, hot and cold plates, associated wiring and the like are contained within the hollow piston 16 as described. These components are preferably encased in a suitable resin or potting material compatible with human tissue. The electrode signal is conducted by conductor 30 which contains a plurality of suitable flexible conductors typically 0.02 mm in diameter. The thermal probe provides a quantitative realtime recording of the regional cortical blood flow. Blood flow increments cool the heated plate and warm the cold plate causing a decrease in output voltage. The voltage is correlated to blood flow according to an established calibration curve as discussed in the earlier patent.

The hydrogen clearance method also carried out by the probe employs hydrogen sensitive pologrphic electrodes or plates 102 and 103 of platinum to develop current proportional to the partial pressure of the hydrogen in the surrounding tissue. Hydrogen may be administered to the patient in various ways such as by inhalation. When hydrogen administration is stopped and its concentration in arterial blood flow goes to zero, the clearance rate of hydrogen from the tissue is reflected as a proportionate decline in current from the electrode, and is determined by local blood flow. If the clearance curve is monoexpedential, blood flow may be calculated by the formula: where F equals blood flow in millileters per gram per minute. Gamma ( ) is the blood tissue partition coefficient which for hydrogen is 1 and $T\frac{1}{2}$ is the half time in minutes of the hydrogen clearance curve. The polaragraphic technique, because it measure current resulting from an imposed voltage, is conceptually an electrode impedance measuring system.

The hydrogen clearance technique uses polaragraphic electrodes 102 and 103 which are common with the thermal diffusion circuit as seen in FIG. 4. Electrode or contact plate 103 is connected to the terminal of polarizing battery 150, the other terminal of which is grounded and connected to the positive input of a high impedance, high gain operational amplifier 155. The output of amplifier 155 is fed to an appropriate monitor 175. The negative input of amplifier 155 is connected to the reference electrode 102 and fed back to the operational amplifier output through resistor 160. Any current flow from the reference electrode or plate 102, which changes the potential of the negative input with respect to ground, will result in current from the amplifier 155 feeding back to bring the negative input to the ground potential. Thus, the electrode 103 is clamped to ground although there is not direct connection between plate 103 and ground. The output of the amplifier 155 then represents the current flow through the electrode 102 and the value of 160 determines the gain of the operational amplifier.

The signal from the operational amplifier 155 is transmitted to the hydrogen clearance monitor 175. Typically, the hydrogen clearance monitor would be a Grass polygraph Model 7 curve digitized by an on-line calculator such as Hewlett-Packard Model 9815A. This data may be further fed into a computer and plotter such as a Textronics 4052 computer and a 4622 Digital plotter. Flow may be calculated by a monoexponental least squares program and the function plotted to check the fit of the curve to the date. The polaragraphic technique, because it measures current resulting from an imposed voltage, is essentially an electrode impedance measuring system.

The following description of the use of the probe of the present invention will be of assistance in understanding the invention.

For detecting internal pressure and blood flow in the skull 19, a burr hole for inserting the probe is provided in a selected portion of the skull, generally with the center axis of the hole being in alignment with the center point of the skull. Sine the thickness of the skull varies with the patient, the probe has sufficient thread depth at 18 to accomodate various thicknesses. The burr hole is drilled and thereafter the probe casing 12 screwed in place with the hexnut cap 24 removed. This allows the attending physicians to peer into the skull and view the surface of the brain or the dura 22 when placing the probe: The probe is screwed to an appropriate depth using hexnut surface 64 until the bottom edge of the casing in in alignment with the interior of the skull as seen in FIG. 2. The piston 16 is then placed in the probe bore 15 with the lower surface of the piston and the associated contact plates 102 and 103 in contact with the dura. The hexnut 24 is put in place with the wire housing interposed between the hexnut and the housing. The wire connector 30 extending through the cap are connected to the suitable monitoring components as described above. The pressure port 62 is connected to a suitable remote pressure sensing device. Saline solution may be placed in the probe and in fluid lines connecting to the port 62 to provide a fluid filled system. With the piston in this position, the electrode plates 102 and 103 are in contact with the surface of the brain to facilitate blood flow measuring by both thermal and hydrogen clearance techniques. Movement of the dura as result of changes in internal pressure in the skull will be accomodated by movement of the piston 50 within the bore. The plates 102 and 103 maintain contact with the dura at all times.

Further, the pressure of the CSP fluid is measured via the pressure port 62 as the fluid pressure is transmitted through the flow passages 58 in the pistons and the pressure port to be monitored externally.

Simultaneously, blood flow is monitored both at monitor 100 and at the hydrogen clearance monitor 175. The hydrogen clearance monitor provides calibration of the quantitative measurement and physicians are thus provided with a continous assessment of local cortical blood flow by simultaneous methods.

Figure 6:
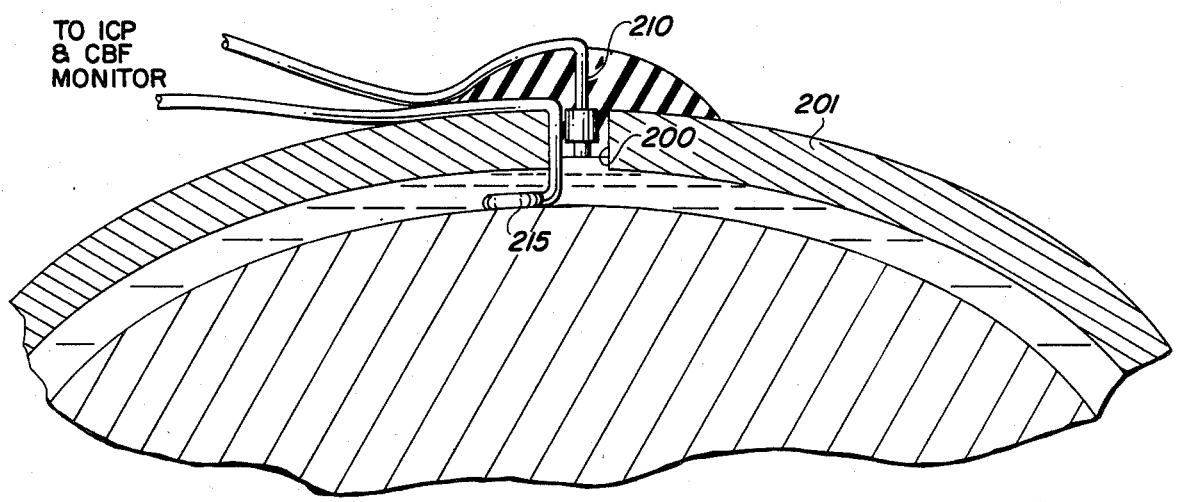
FIG. 6 illustrates an alternate embodiment of the combined pressure and blood flow probe.

FIG. 6 illustrates another embodiment of the present invention in which blood flow and intracranial pressure is measured at burr hole 200 in skull 201. Here pressure is determined by a pressure probe 210 extending into the hole 200 a preselected distance and held in position by a suitable adhesive substance such as silicone rubber. Pressure probe 210 is a transducer for sensing and measuring pressure, as for example, the type manufactured by Thermometrics, Inc. and designated the PPS-1 designed for biomedical use.

Flow is sensed at flow probe 215 which may be electrodes for hydrogen clearance or thermal diffusion as described above and connected as shown in FIG. 4 to appropriate operational and monitoring equipment and circuitry.

It will be obvious to those skilled in the art to make various changes, alterations or modifications to the invention described herein. To the extent that these variations, changes or modifications do not depart from the spirit and scope of the appended claims, they are intended to be encompassed therein.

I claim:

1. An intracranial probe for measuring local cerebral blood flow and intracranial pressure comprising:
   (a) a casing defining a generally cylindrical bore, said casing having an exterior portion for securement to the skull of a body and further including a pressure port communicating with said bore and adapted to communicate pressure to a remote pressure monitor;
   (b) a piston reciprocal in said bore;
   (c) a first platinum-containing contact plate forming at least a portion of said piston;
   (d) a second platinum-containing contact plate forming at last a portion of said piston;
   (e) first signal means coupled to said first contact plate for outputting a signal proportional to the temperature of the first plate;
   (f) second signal means coupled to said second contact plate for outputting a signal proportional to the temperature of said second plate, said first and second means adapted to be connected to comparative means;
   (g) first conductor means connected to said first plate;
   (h) second conductor means connected to said second plate, said first and second conductor means adapted to be connected to polygraph means to monitor current generated by said plates; and
   (i) means for polarizing said contact plates whereby said probe is securable in said skull with the said portions of the piston adapted to be in contact with the dura for measuring local cerebral blood flow by both thermal and hydrogen clearance techniques and means associated with said piston communicating a pressure signal indicative of intracranial pressure whereby the internal pressure is communicated across said piston to said bore to said pressure port.

2. The probe of claim 1 having a thermoelectric heat pump coupled to said contact plates.

3. The probe of claim 2 having power supply means coupled to said heat pump for providing the necessary drive to power the heat pump.

4. The probe of claim 1 wherein said casing is provided with a removable cap and said piston is removable from the bore of said casing.

5. The probe of claim 1 wherein said casing is provided with an exterior surface adapted to receive a tightening tool.

6. The probe of claim 1 wherein said signal means and said conductor means are incorporated in a single cable connected at said piston.

7. The probe of claim 6 wherein said single cable exerts a biasing force on said piston.

8. The probe of claim 1 wherein said piston defines flow passages.

9. The probe of claim 1 further including signal conditioning means and a microprocessor based control unit operationally connected to one another and to said contact plates.

10. The probe of claim 1 including temperature transducer means encased within said piston.

11. A method of measuring intracranial pressure and blood flow in a patient comprising:
    (a) placing a probe in the skull of the patient having temperature transducer and contact plates therein adapted to contact a portion of the brain and float to maintain contact therewith;
    (b) establishing a voltage proportional to the temperature difference between the contact plates and determining blood flow therein by thermal difference;
    (c) administering hydrogen to the patient;
    (d) polarizing said contact plates;
    (e) measuring the hydrogen clearance ratio by determining the decline in current in said control plate; and
    (f) simultaneously monitoring intracranial pressure along with the thermal difference and hydrogen clearance measurement.

* * * * *